United States Patent
Thomas et al.

(10) Patent No.: US 9,980,790 B2
(45) Date of Patent: May 29, 2018

(54) DENTAL VALVE DEVICE HAVING A DISPOSABLE TURRET

(71) Applicant: Stoma Ventures, LLC, St. Louis, MO (US)

(72) Inventors: Charles Thomas, Vero Beach, FL (US); Edward Arguello, Weston, FL (US)

(73) Assignee: STOMA VENTURES, LLC, Chesterfield, MO (US)

( * ) Notice: Subject to any disclaimer, the term of this patent is extended or adjusted under 35 U.S.C. 154(b) by 200 days.

(21) Appl. No.: 15/082,069

(22) Filed: Mar. 28, 2016

(65) Prior Publication Data

US 2017/0273756 A1   Sep. 28, 2017

(51) Int. Cl.
*A61C 1/00* (2006.01)
*A61C 17/06* (2006.01)

(52) U.S. Cl.
CPC ............ *A61C 1/0061* (2013.01); *A61C 17/04* (2013.01)

(58) Field of Classification Search
CPC ..... A61C 1/0061; A61C 17/04; F16K 5/0407; F16K 15/144; F16K 15/185; F16K 15/188; A61M 2039/244; A61M 2205/0202
See application file for complete search history.

(56) References Cited

U.S. PATENT DOCUMENTS

| | | | |
|---|---|---|---|
| 3,474,818 A * | 10/1969 | Hartman | F16K 5/045 137/269.5 |
| 4,797,098 A | 1/1989 | Kawata | |
| 4,989,631 A * | 2/1991 | Harbin | F16K 5/0407 137/15.07 |
| 5,295,830 A | 3/1994 | Shen et al. | |
| 5,464,350 A | 11/1995 | Bierbaum | |
| 5,725,374 A | 3/1998 | Young | |
| 8,256,464 B2 | 9/2012 | Bushman et al. | |
| 8,763,638 B2 | 7/2014 | Deubler | |
| 2003/0052193 A1* | 3/2003 | Shanklin | B05B 7/1209 239/318 |
| 2003/0219696 A1 | 11/2003 | Moreland | |
| 2008/0289696 A1 | 11/2008 | Bushman | |
| 2012/0305100 A1 | 12/2012 | Bushman et al. | |
| 2014/0170595 A1* | 6/2014 | Williams | A61C 17/04 433/95 |
| 2014/0239551 A1* | 8/2014 | Williams | A61C 17/04 264/328.13 |
| 2015/0144208 A1* | 5/2015 | Caccavo | F16K 35/025 137/512.2 |

\* cited by examiner

*Primary Examiner* — Nicholas Lucchesi
(74) *Attorney, Agent, or Firm* — David H. Chervitz

(57) ABSTRACT

A dental valve device having a disposable turret is disclosed having a valve body having a tip receiving end, a hose receiving end, a lumen formed between the tip receiving end and the hose receiving end, an opening formed in the valve body, and a rotatable valve sealing body adapted to being inserted into the opening, the rotatable valve sealing body having a bore for alignment with the lumen formed between the tip receiving end and the hose receiving end, the bore having a tip receiving end opening and a hose receiving end opening, the rotatable valve sealing body having an outer surface having an indentation formed in the outer surface adjacent to the tip receiving end opening with the indentation having an upper ramp portion, a lower ramp portion, and an end having a tab portion.

14 Claims, 9 Drawing Sheets

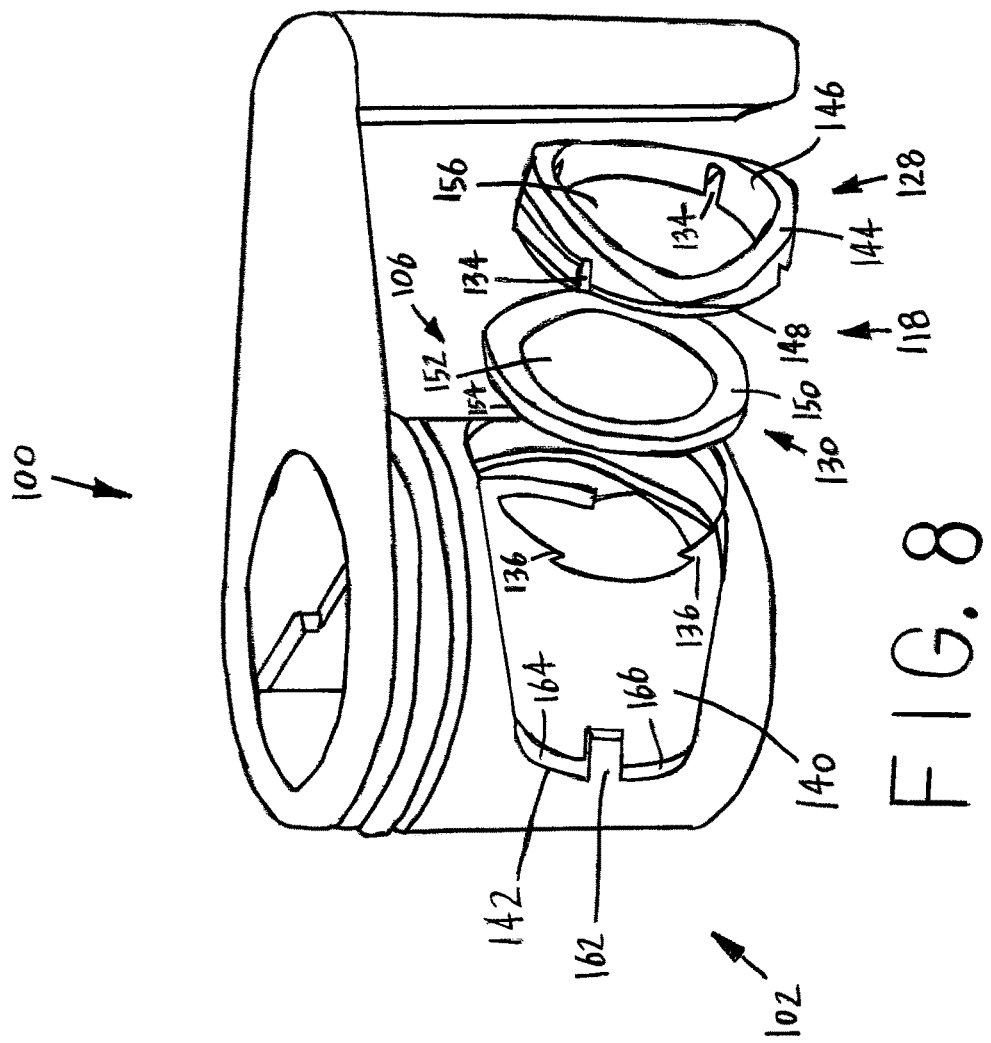

DENTAL VALVE DEVICE HAVING A DISPOSABLE TURRET

BACKGROUND

This disclosure relates to a dental valve device for a dental instrument for removing saliva, other fluids, and debris from a mouth of a patient and more particularly to a dental valve device having a disposable turret.

During a dental procedure it is important to be able to remove saliva, blood, water, tooth fragments, metals, and other debris or fluids from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector or a low volume ejector. A saliva ejector typically comprises a plastic flexible tube for placement in the mouth of a patient. The saliva ejector tube is connected to a valve which in turn is connected via suction tubing to a source of vacuum. In this manner, saliva is passed through the ejector tube, the valve, and the tubing to be disposed of in a sanitary manner. Once the procedure is completed, the ejector should be discarded and the valve should be sterilized by autoclaving to be used again. Although it is suggested to autoclave the valve after each use, it is known that autoclaving is hardly ever done. Another device that is capable of removing solid materials is a high volume evacuator system. A high volume evacuator system generally consists of a tube that may be inserted into a mouth of a patient with the tube connected to a high volume evacuator valve which is connected via a tubing to a source of vacuum. Again, in this manner, debris may be removed from the mouth of the patient. After the dental procedure, the tube is disposed of and the valve should be sterilized for reuse. However, although it is suggested to sterilize the valve after use, it is known that this suggested procedure is hardly ever followed. The high volume evacuator valve is typically larger than the saliva ejector valve due to the high volume evacuator valve having to remove large debris from the mouth of a patient.

The saliva ejector valve and the high volume evacuator valve each has a valve body having a passage and a valve sealing member or movable turret. The turret has an opening that may be aligned with the passage to allow saliva and other material to pass when the turret is in an open position. When the turret is in a closed position, the source of vacuum is cut off by the turret blocking the passage through the valve body. In this manner, the saliva ejector valve and the high volume evacuator valve may be opened or closed. The valves invariably collect debris, body fluids, blood, and solids that adhere and accumulate upon the internal surfaces of the valve. The detritus that adheres to the internal surfaces of the valve body and the turret can become a breeding ground for microbial contaminants. This buildup also contains microorganisms that remain in the valve system unless the valves are disassembled, the internal accumulated debris removed, and the valve body and the turret sterilized.

As can be appreciated, if the valve is not cleaned and sterilized after each procedure there is the possibility of cross-contamination from one patient to another patient. In order to control infection and disease, the valve must be removed from service, disassembled, cleaned, sterilized, reassembled, checked, and then returned to service. To complicate matters, the valve may have various O-rings that need to be replaced in order for the valve to function properly. For example, the turret may include two O-rings that assist in holding the turret within the opening formed in the valve body. When disassembling the turret from the valve body, it is possible that the O-rings may become damaged. If this were to occur then the O-rings would have to be replaced. It is also possible that the O-rings may deteriorate over time and air may leak through the opening and the turret. If this were to occur then it is possible that the valve and the turret may malfunction during a dental procedure or operation. For example, the turret may be ejected from the valve body and any saliva, liquid, blood, or debris may spray out of the opening where the turret should be sealing the valve. Malfunctioning of the valve during an operation should be avoided because the operation will have to be paused or stopped and the operating room will have to be cleaned.

As pointed out above, a further disadvantage associated with the use of these known valves is that there is the possibility of cross-contamination between patients and/or dental care professionals. In order to prevent cross-contamination it becomes necessary to process these valves by cleaning and decontamination. Cleaning requires that the valve be dissembled so that all of the debris be removed from the valve as well as any organic and inorganic contamination. Removal of debris and contamination may be achieved either by scrubbing with a surfactant, detergent, and water, or by an automated process using chemical agents. One example of an automated process is the use of an ultrasonic cleaner. The valve also needs to be sterilized after debris and contaminants are removed. Since the valves are constructed of metal they are heat-tolerant and may be sterilized by use of such methods such as steam under pressure (autoclaving), dry heat, or unsaturated chemical vapor. As can be appreciated, protecting against cross-contamination can be an expensive and time consuming proposition. Further, as noted above, the valves contain a number of O-rings that may need to be replaced. In order to accomplish this, an inventory of O-rings needs to be maintained. Also, in order to replace some of the O-rings, a lubricant may have to be used. Again, the lubricant will have to be inventoried so that a supply is readily available for use by service technicians. Having to inventory various supplies that may be required to service such valves is a cumbersome operation that many healthcare facilities may want to avoid.

As indicated, the saliva ejector and the high volume evacuator are used to remove liquids and debris from a mouth of a patient to prevent a patient from swallowing or aspirating liquids and debris produced during a dental procedure. Typically, when using these evacuator devices there is no backflow back into the mouth of a patient. However, there are times when backflow or a reverse flow may take place and previously removed liquids and debris may flow back into the mouth of the patient. It is also possible that if the systems are not properly maintained that fluids and debris from a previous patient may flow back into the mouth of a subsequent patient. These situations may be dangerous, are undesirable, and should be avoided.

In order to prevent backflow, there are various devices that are separate from the saliva ejector. These devices are inserted between the flexible tube and the dental valve or between the dental valve and suction tubing. These devices tend to be complex and expensive. Further, these devices have to be separately purchased, inventoried, and used apart from the flexible tube and the dental valve.

Therefore, it would be desirable to have a dental valve device device having a disposable turret in which the turret may be disposable and a valve body associated with the dental valve device may be reused. It would also be useful to have a dental valve device that has a disposable turret that incorporates a check valve in the disposable turret for preventing a backflow condition.

BRIEF SUMMARY

In one form of the present disclosure, a dental valve device is disclosed comprising a valve body having a tip receiving end, a hose receiving end, a lumen formed between the tip receiving end and the hose receiving end, an opening formed in the valve body, and a rotatable valve sealing body adapted to being inserted into the opening formed in the valve body, the rotatable valve sealing body having a bore for alignment with the lumen formed between the tip receiving end and the hose receiving end, the bore having a tip receiving end opening and a hose receiving end opening, the rotatable valve sealing body having an outer surface having an indentation formed in the outer surface adjacent to the tip receiving end opening with the indentation having an upper ramp portion, a lower ramp portion, and an end having a tab portion.

In another form of the present disclosure, a dental valve device comprises a valve body having a tip receiving end, a hose receiving end, a lumen formed between the tip receiving end and the hose receiving end, an opening formed in the valve body, and a rotatable valve sealing body adapted to being inserted into the opening formed in the valve body, the rotatable valve sealing body having a bore for alignment with the lumen formed between the tip receiving end and the hose receiving end, the bore having a tip receiving opening and a hose receiving opening, a check valve, the rotatable valve sealing body having an outer surface having an indentation formed in the outer surface adjacent to the tip receiving end opening with the indentation having an upper ramp portion, a lower ramp portion, and an end having a tab portion.

In yet another form of the present disclosure, a dental valve device comprises a valve body having a tip receiving end, a hose receiving end, a lumen formed between the tip receiving end and the hose receiving end, and an opening formed in the valve body, and a rotatable valve sealing body adapted to being inserted into the opening formed in the valve body, the rotatable valve sealing body having a bottom having an opening, a bore for alignment with the lumen formed between the tip receiving end and the hose receiving end, the bore having a tip receiving end opening and a hose receiving end opening, the rotatable valve sealing body having a check valve positioned in the bore and the opening in the bottom, the rotatable valve sealing body having an outer surface having an indentation formed in the outer surface adjacent to the tip receiving end opening with the indentation having an upper ramp portion, a lower ramp portion, and an end having a tab portion.

The present disclosure provides a dental valve device having a disposable turret for use with a dental instrument in which the disposable turret is suitable for one time use and may be discarded after a single use and a valve body associated with the dental valve device being reusable.

The present disclosure is directed to a dental valve device having a disposable turret that does not require any O-rings.

The present disclosure provides a dental valve device having a disposable turret that is easy to install into or remove from a valve body.

The present disclosure provides a dental valve device having a disposable turret that is small, lightweight, easy to handle, easy to install, and easy to operate.

The present disclosure also provides a dental valve device having a disposable turret which is of simple construction and design and which can be easily employed with highly reliable results.

The present disclosure is related to a dental valve device having a disposable turret in which the disposable turret does not require sterilization and prevents against any cross-contamination.

The present disclosure is related to a dental valve device having a disposable turret in which the disposable turret does not require sterilization and prevents against any backflow and cross-contamination.

The present disclosure provides a dental valve device having a disposable turret that may have an antimicrobial agent or chemical incorporated into the disposable turret to prevent any bacterial growth on the device. The antimicrobial agent or chemical may also be a coating applied to the disposable turret.

The present disclosure is related to a dental valve device having a disposable turret that may be constructed of plastic that is recyclable or biodegradable to reduce the cost of the disposable turret and to allow the disposable turret to be disposable and discarded after a single use.

The present disclosure is further related to a dental valve device having a disposable turret that is easy to manipulate during a dental operation to open or close the dental valve device.

The present disclosure is related to a dental valve device having a disposable turret that is easy to manipulate during a dental operation to open or close the valve and the disposable turret also incorporating a check valve to automatically prevent backflow of saliva, liquid, or other material.

The present disclosure is further directed to a dental valve device having a disposable turret that allows a dental tip to be inserted into the disposable turret to reduce any surface area that may be contaminated.

The present disclosure is also related to a dental valve device having a disposable turret with the dental valve device having a reusable valve body and the valve body having fewer surfaces that need to be cleaned or sanitized.

These and other advantages of the present disclosure will become apparent after considering the following detailed specification in conjunction with the accompanying drawings, wherein:

BRIEF DESCRIPTION OF THE DRAWINGS

FIG. 8 is a perspective view of the disposable turret constructed according to the present disclosure with the check valve removed from the disposable turret and shown in an exploded view;

DETAILED DESCRIPTION OF PREFERRED EMBODIMENTS

Figure 1:
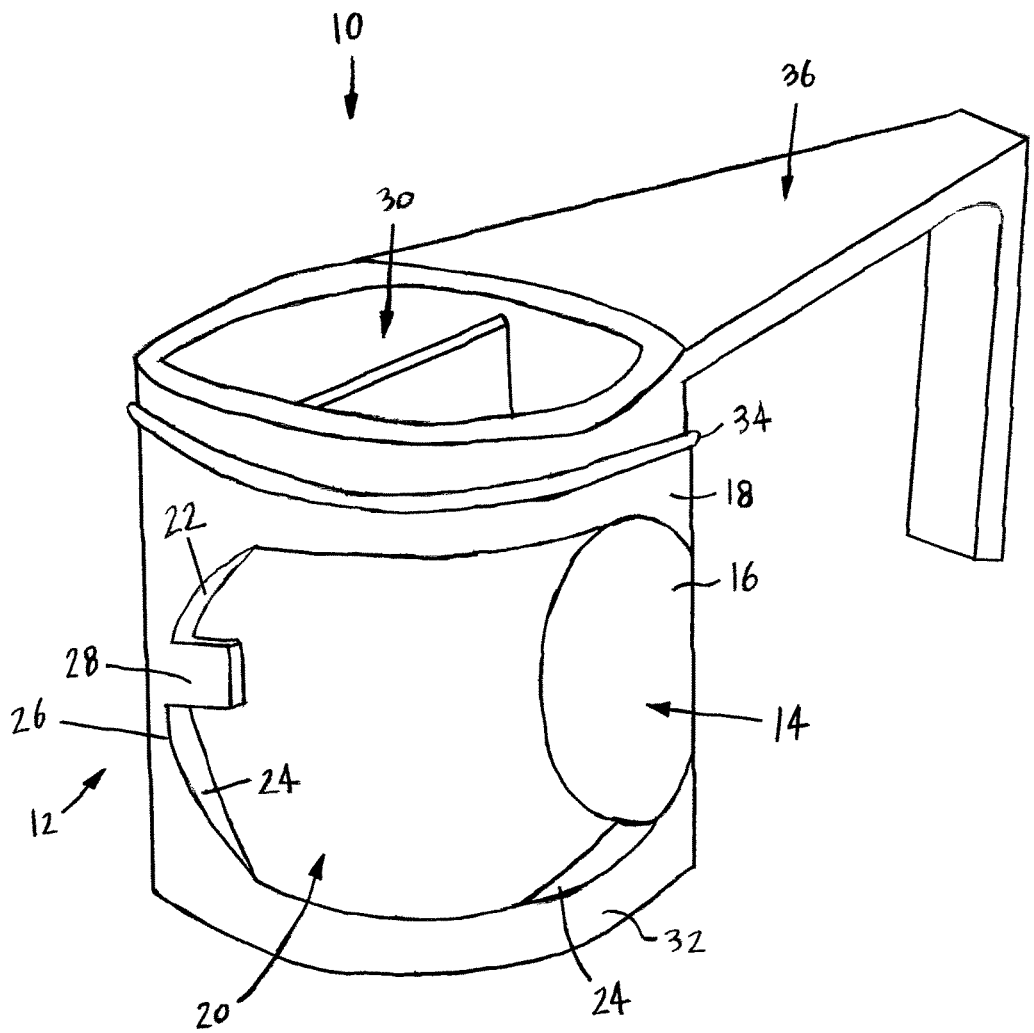
FIG. 1 is a perspective view of a disposable turret for a dental valve device constructed according to the present disclosure.

Referring now to the drawings, wherein like numbers refer to like items, number 10 identifies a disposable turret for a dental valve device for use with a dental system (not shown) constructed according to the present disclosure. With reference now to FIG. 1, the disposable turret 10 comprises a rotatable valve sealing body 12 adapted to being inserted into a valve body (not shown) with the rotatable valve sealing body 12 having a bore 14 having a tip receiving end opening 16, an outer surface 18 having an indentation 20 formed in the outer surface 18 adjacent to the tip receiving end opening 16 with the indentation 20 having an upper ramp portion 22, a lower ramp portion 24, and an end 26, such as a rounded end. The indentation 20 is used to capture an evacuator tip device or a dental tip (not shown) such as a saliva ejector tip. The ramp portions 22 and 24 allow the dental tip to slide within the indentation 20 and out of the way when the disposable turret 10 is operated. The indentation 20 also facilitates scraping any debris (not shown) away from the dental tip. The end 26 also has a detent or tab portion 28 that is used to assist in ejecting the dental tip out of the indentation 20 and the dental valve device. The disposable turret 10 also has a top 30, a bottom 32, and an annular ridge portion 34 formed near the top 30. Although only one annular ridge portion 34 is shown, it is possible that another annular ridge portion may be formed near a bottom 32 of the disposable turret 10. The rotatable valve sealing body 12 also has a handle portion 36 connected to or a part of the top 30. Although the handle portion 36 is shown, it is also possible and contemplated that the top 30 of the disposable turret 10 may be used to rotate the disposable turret 10.

Figure 2:
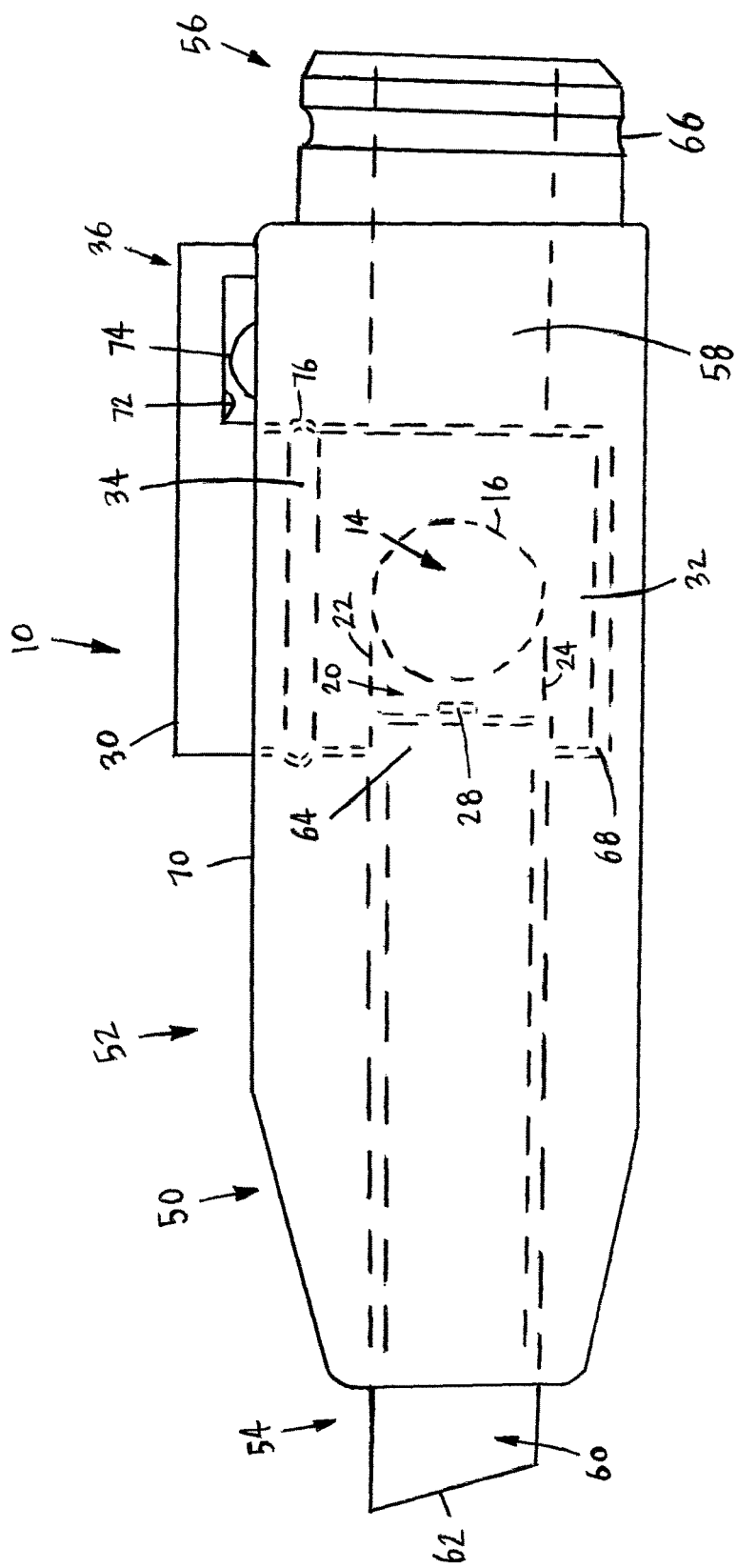
FIG. 2 is a side view, shown partially in phantom, of a disposable turret for a dental valve device being inserted into a valve body of the dental valve device.

FIG. 2 shows the disposable turret 10 being inserted into a valve body 50 with the disposable turret 10 and the valve body 50 forming a dental valve device 52. The valve body 50 has a tip receiving end 54, a suction tubing or hose receiving end 56, and a lumen 58 formed within the valve body 50 between the end 54 and the end 56. The tip receiving end 54 is adapted for receiving an evacuator tip device 60, such as a high volume evacuator tip or a low volume evacuator (saliva ejector) tip. The hose receiving end 56 is adapted to receive a vacuum line or a hose (not shown) which is connected to a suction system (also not shown) which is used to dispose of any saliva, liquid, or debris removed from a mouth of a patient. The evacuator tip device 60 has a front end 62 which may be inserted into a mouth of a patient and a rear end 64 that is inserted into the lumen 58. The hose receiving end 56 also has a circumferential channel 66 that is adapted to accept an O-ring (not shown). The O-ring is used to further secure a hose or a tailpiece to the hose receiving end 56. It is also possible that the hose receiving end 56 may incorporate a structure to secure a hose to the end 56 without the use of the channel 66 or the requirement for an O-ring. For example, the end 56 may be barbed so that the barbs may hold a hose thereon. The valve body 50 also has an opening 68 formed on a top side 70 of the valve body 50 in which the disposable turret 10 is inserted. The opening 68 is a partial opening in that it does not go all the way through the valve body 50.

The disposable turret 10 is constructed of material that allows the disposable turret 10 to be disposable and suitable for one time use. The valve body 50 may be constructed of metal which can be cleaned and sanitized once the disposable turret 10 has been removed and discarded. The valve body 50 may be reused once cleaned and sanitized. As can be appreciated, once the valve body 50 is cleaned and sanitized, a new disposable turret 10 may be inserted into the opening 68. The disposable turret 10 also has the handle 36 for manual operation of the disposable turret 10 of the dental valve device 52. The handle 36 also has a tab portion or bump 72 and the valve body 50 also has a tab portion or bump 74 formed on the top side 70. The tab portions 72 and 74 are used to contact each other to assist in removing or forcing the disposable turret 10 out from within the opening 68 of the valve body 50. Manual operation of the handle 36 will open the device 52, close the device 52, or partially open the device 52. As can be appreciated, a suction system provides suction through the evacuator tip device 60, the valve body 50, the disposable turret 10, and a hose so that any debris, liquid, or saliva that is introduced into the evacuator tip device 60 is removed through the evacuator tip device 60, the valve body 50, the disposable turret 10, and a hose when the disposable turret 10 is in an open state or a partially open state.

Although not shown, it is contemplated that the tip receiving end 54 may be constructed having an interior annular ring for receiving an O-ring to retain the evacuator tip device 60 therein. It is also possible that the tip receiving end 54 may have other structure that will allow a frictional engagement of the evacuator tip device 60 within the tip receiving end 54. The opening 68 is shown being a partial opening, but it is possible that the opening may be formed to extend completely through the valve body 50. The opening 68 has an annular ring or channel 76 formed therein and the channel 76 is used to capture the annular ridge portion 34 to retain the disposable turret 10 within the opening 68 without the use of an O-ring. The rear end 64 of the evacuator tip device 60 is shown being captured within the indentation 20 of the disposable turret 10. The bore 14 having the tip receiving end opening 16 and the handle portion 36 are also shown. In this particular view, the disposable turret 10 is depicted being in a closed position. The disposable turret 10 may be moved to an open position by aligning the bore 14 with the lumen 58. Further, because the rear end 64 of the evacuator tip device 60 is received within the indentation 20, no debris, saliva, or other matter is capable of forming or being trapped in the lumen 58 where the evacuator tip device 60 is. This means that less area within the lumen 58 can be contaminated and less time will be required in cleaning and sanitizing the valve body 50. Also, the indentation 20 also assists in scraping any debris or other material from the rear end 64 of the evacuator tip device 60 into the bore 14 of the disposable turret 14. Again, this reduces the surface area within the lumen 58 that may be contaminated. The tab portion 28 is used to assist in pushing the rear end 64 of the evacuator tip device 60 forward and out of the lumen 58 when the valve body 50 needs to be cleaned. The tab portion 28 also functions to release the rear end 64 from being within the indentation 20.

Figure 3:
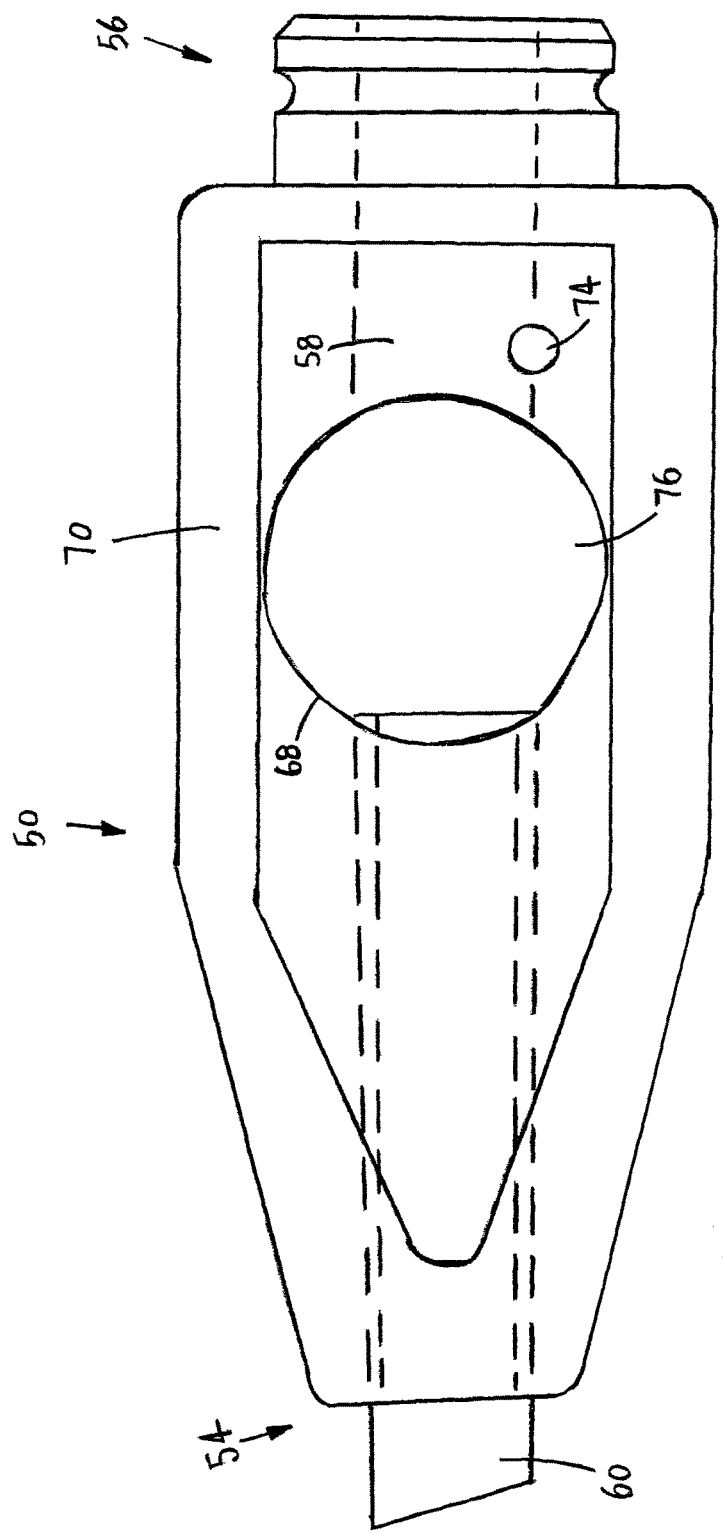
FIG. 3 is a top view, shown partially in phantom, of a valve body of a dental valve device with a disposable turret being removed from the valve body of the dental valve device.

With reference now to FIG. 3, the valve body 50 having the disposable turret 10 removed is illustrated. The valve body 50 has the tip receiving end 54, the suction tubing or hose receiving end 56, and the lumen 58 formed within the valve body 50 between the ends 54 and 56. The top side 70 has the opening 68 formed therein and the tab portion 74 positioned on the top side 70. The valve body 50 also has a bottom 76 shown through the opening 68. The tip receiving end 54 is shown receiving the evacuator tip device 60 therein. As has been previously discussed, the valve body 50 may be constructed of metal and the valve body 50 is intended for numerous uses. Further, the evacuator tip device 60 is a single use or disposable product.

Figure 4:
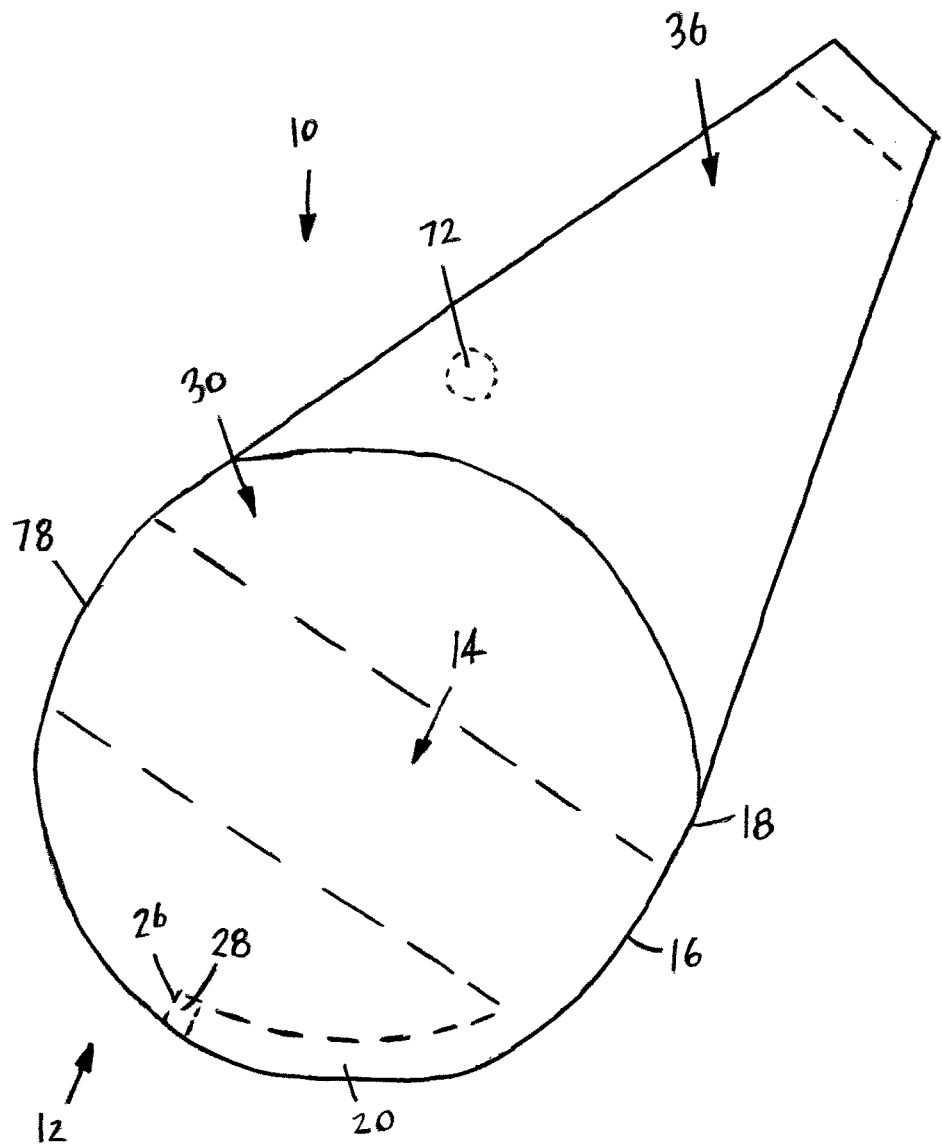
FIG. 4 is a top view of a disposable turret, shown partially in phantom, being removed from a valve body of a dental valve device.

FIG. 4 shows a top view of the disposable turret 10, partially in phantom, being removed from the valve body 50. The disposable turret 10 has the rotatable valve sealing body 12 adapted to being inserted into a valve body, such as the valve body 50 shown in FIGS. 2 and 3, with the rotatable valve sealing body 12 having the bore 14 having the tip receiving end opening 16, the outer surface 18 with the indentation 20 formed in the outer surface 18 adjacent to the tip receiving end opening 16. The rotatable valve sealing body 12 also has the top 30 and the handle portion 36 connected to the top 30. The indentation 20 spans from the tip receiving end opening 16 to the end 26. The tab portion 28 is also shown extending out from the end 26. The disposable turret 10 also has a hose receiving end opening 78 formed in the outer surface 18. The hose receiving end opening 78 is aligned with the bore 14 and allows any saliva or debris to pass through the opening 78. The tab portion 72, which extends out from the handle portion 36 is also shown.

Figure 5:
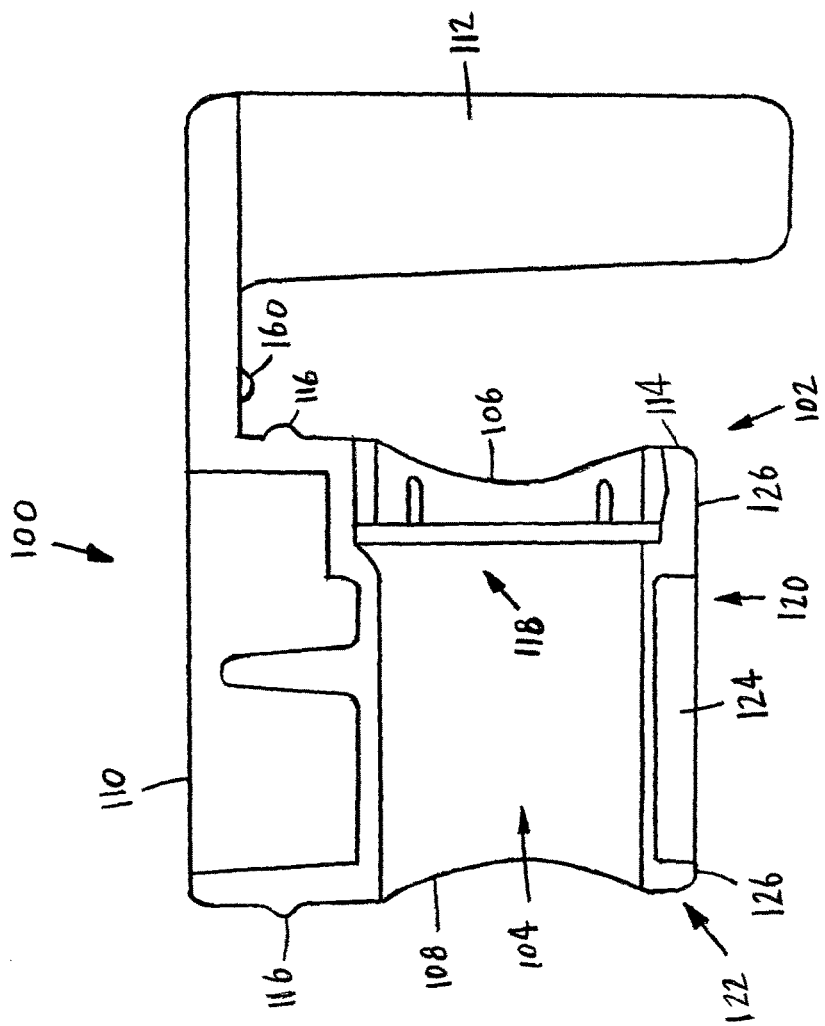
FIG. 5 is a cross-sectional view of another embodiment of a disposable turret for a dental valve device being removed from a valve body of the dental valve device with a check valve in a closed position.

With particular reference now to FIG. 5, a cross-sectional view of another embodiment of a disposable turret 100 is shown. The disposable turret 100 is adapted to be inserted into a valve body, such as the valve body 50. The disposable turret 100 comprises a rotatable valve sealing body 102 having a bore 104 having a tip receiving end opening 106 and a hose receiving end opening 108. The rotatable valve sealing body 102 also has a top 110 and a handle portion 112 connected to the top 110. Although not shown in this particular view, the disposable turret 100 also has an indentation formed in an exterior surface 114. An annular ridge portion 116 is formed near the top 110. The annular ridge portion 116 is capable of fitting into the channel 76 (FIG. 2) in a snap fit engagement to secure the disposable turret 100 in the valve body 50. The tip receiving end opening 106 has a check valve 118 positioned therein to selectively open or close the tip receiving end opening 106. The check valve 118 is provided for allowing liquid, saliva, or debris to pass from the tip receiving end opening 106, the check valve 118, the bore 104, and out the hose receiving end opening 108 when the check valve 118 is opened. In this manner, fluid, saliva, and debris may be removed from a mouth of a patient during a dental procedure or operation. However, the check valve 118 also prevents any liquid, saliva, or debris from passing or traveling from the hose receiving end opening 108, the bore 104, and through the check valve 118 when the check valve 118 is closed. The check valve 118 will close when a reduced pressure occurs from an interaction of a mouth of a patient on an evacuator tip device. For example, a patient may be requested to close the mouth of the patient around the evacuator tip device. When this occurs, a reduced pressure results in which a backflow may occur. The check valve 118 is sensitive to this pressure differential and will close to prevent backflow. The check valve 118 is shown in the closed position in FIG. 5. The handle portion 112 has a tab portion 160 that is used to contact the tab portion 74 associated with the valve body 50.

Although only the single annular ridge portion 116 is shown, it is possible that another annular ring may be formed in the rotatable valve sealing body 102 to hold the body 102 in place. The other annular ridge portion may be formed on the body 102 near a bottom 120 of the body 102.

The rotatable valve sealing body 102 also has an annular ring 122 formed in the bottom 120. A central indentation 124 is formed within the annular ring 122. The annular ring 122 has a surface 126 that contacts an interior surface (not shown) of the bottom 74 (FIG. 3) of the valve body 50 (FIGS. 2 and 3). The annular ring 122, the central indentation 124, and the surface 126 facilitate smooth and easy rotation of the rotatable valve sealing body 102 within the valve body 50. The annular ring 122, the central indentation 124, and the surface 126 further allow rotation of the body 102 without being bound up within the valve body 50.

Figure 6:
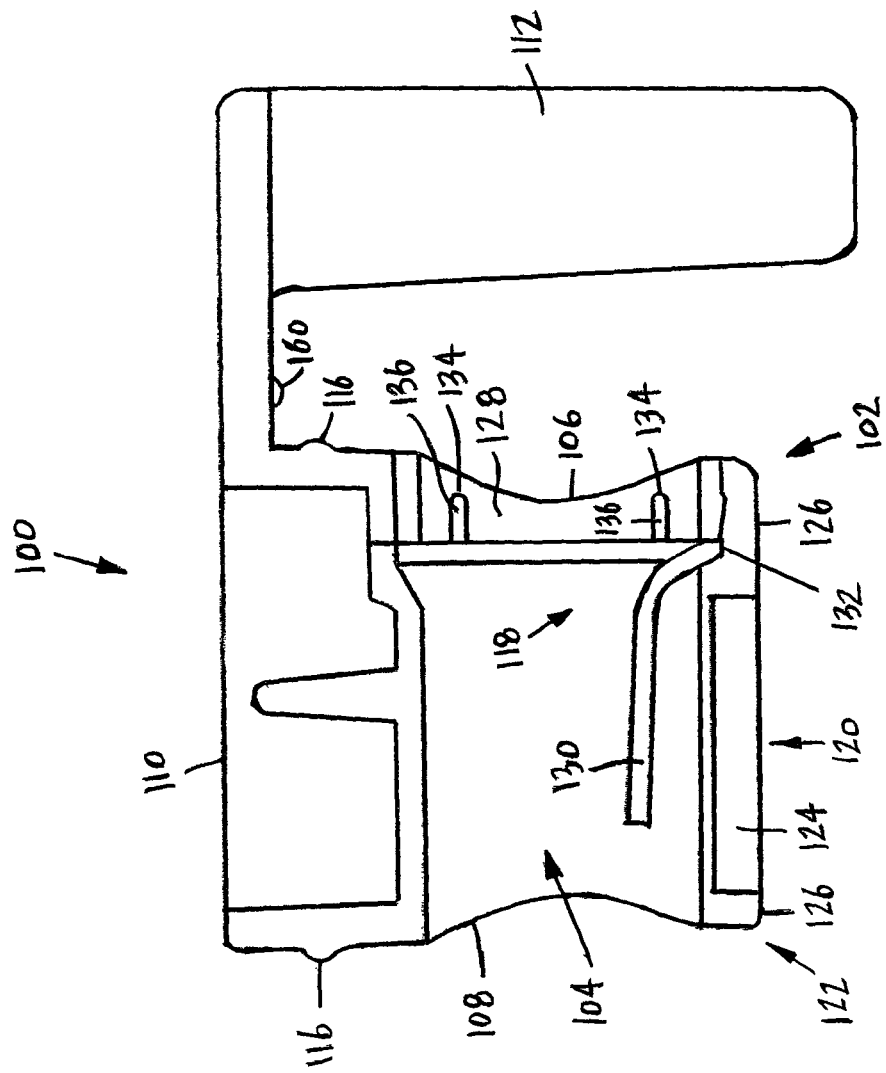
FIG. 6 is a cross-sectional view of the disposable turret shown in FIG. 5 with a check valve in an opened position.

Referring now to FIG. 6, the check valve 118 of the rotatable valve sealing body 102 of the disposable turret 100 is illustrated in the open position. The check valve 118 comprises a housing 128 having a flap portion 130 being connected at an end portion 132. The connection of the flap portion 130 at the end portion 132 allows the check valve 118 to open or close. The end portion 132 may be a hinge device that allows the flap portion 130 to move relative to the housing 128. The housing 128 also has retaining rib openings 134 formed in the housing 128. The rotatable valve sealing body 102 has retaining ribs 136 formed in the tip receiving end opening 106. The openings 134 are used to receive the ribs 136 therein for retaining the check valve 118 in the tip receiving end opening 106. In this manner, a snap fit engagement of the check valve 118 within the tip receiving end opening 106 is provided. Although the openings 134 and the ribs 136 are shown, it is possible that other retention or engagement type constructions are contemplated, such as using an adhesive or forming the check valve 118 and the body 102 as a unitary piece or construction. As can be appreciated, when the flap portion 130 is in the open position the flap portion 130 will only be within the bore 104 of the body 102. The rotatable valve sealing body 102 is also shown having the top 110, the hose receiving end opening 108, the bottom 120, the annular ring 122, the central indentation 124, the surface 126, the handle 112, and the annular ridge portion 116. The openings 106 and 108 are concave and this provides for smooth rotation of the body 102 within the valve body 50 (FIGS. 2 and 3). The handle portion 112 also has the tab portion 160 that is used to contact the tab portion 74 associated with the valve body 50 to assist in removing the valve sealing body 102 out of the valve body 50 for disposal.

Figure 7:
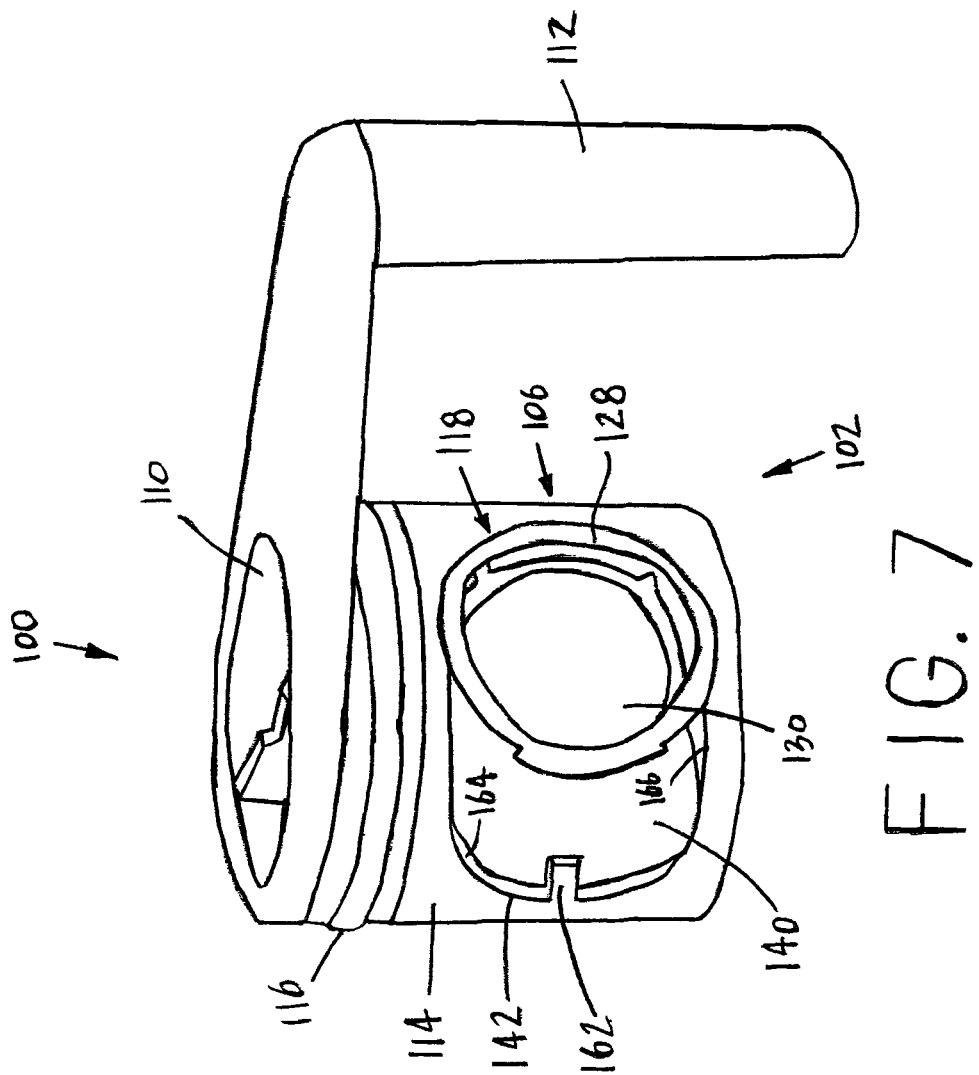
FIG. 7 is a perspective view of the disposable turret constructed according to the present disclosure with the check valve shown in the closed position.

FIG. 7 shows a perspective view of the rotatable valve sealing body 102 of the disposable turret 100 with the check valve 118 in the closed position. The housing 128 is positioned in or on the tip receiving end opening 106. The flap portion 130 is positioned up against the housing 128. With the flap portion 130 in this position, the closed position, no fluid, saliva, or debris will flow through the body 102. The body 102 has the exterior surface 114 having an indentation 140 formed therein. The indentation 140 extends or spans from the tip receiving end opening 106 to an end 142. The end 142 also has a detent or tab portion 162 that is used to assist in ejecting an evacuator tip device (not shown) out of the valve body 50. The indentation 140 also has an upper ramp portion 164 and a lower ramp portion 166. The ramp portions 164 and 166 allow the evacuator tip device to slide within the indentation 140 and out of the way when the disposable turret 100 is operated. The annular ridge portion 116 is positioned near the top 110. Also, the handle 112, which is part of the top 110, is shown extending away from the body 102.

With reference now to FIG. 8, a perspective view of the rotatable valve sealing body 102 of the disposable turret 100 is shown with the check valve 118 removed from the tip receiving end opening 106. The check valve 118 is also depicted in an exploded view in that the housing 128 and the flap portion 130 have been separated. As has been discussed, the housing 128 and the flap portion 130 may be a unitary construction. The housing 128 has a front surface 144 that is concave to follow the concave tip receiving end opening 106 so that the front surface 144 is flush with the exterior surface 114 when the housing 128 is inserted into the tip receiving end opening 106, as is depicted in FIG. 7. The housing 128 also has a center portion 146 and a back 148. The center portion 146 and the back 148 have the openings 134 formed therein. Although four openings 134 are shown, it is contemplated that more or less openings 134 may be provided in the housing 128. The flap portion 130 has a front side 150, a center portion 152, and a back side 154. The front side 150 and the center portion 152 are sized and shaped to fit over the center portion 146 and the back 148 of the housing 128. As can be appreciated, the flap portion 130 is a solid piece and the housing 128 has a central opening 156. The flap portion 130 is used to cover or close the central opening 156. It is also possible that the back 148 may have a recess, groove, or rabbet formed therein to receive or seat the flap portion 130 therein. The flap portion 130 may be connected to the housing 128 in any suitable manner. The tip receiving end opening 106 has the ribs 136 that are used to capture the openings 134 to hold the housing 128 in place in or around the tip receiving end opening 106. Although four ribs 136 are depicted, as with the openings 134, more or less ribs 136 are possible. The body 102 also has the exterior surface 114 having the indentation 140 formed therein. The indentation 140 extends or spans from the tip receiving end opening 106 to the end 142. The indentation 140 also has the tap portion 162 and the ramp portions 164 and 166.

Figure 10:
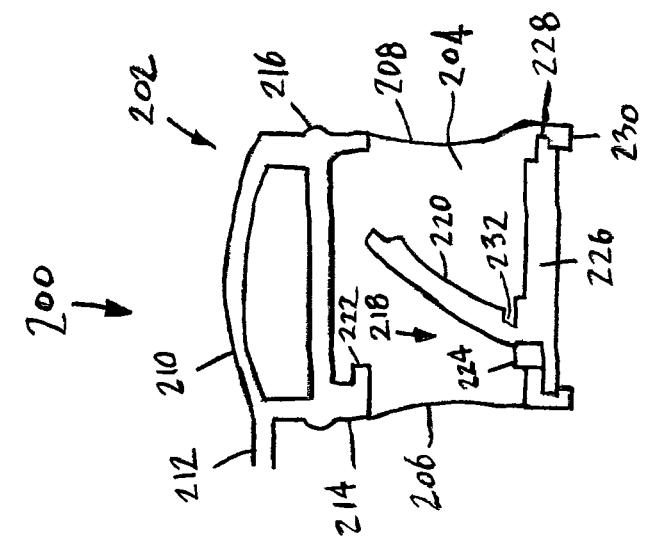
FIG. 10 is a partial cross-sectional view of another embodiment of a disposable turret having a check valve shown in a partially open position constructed according to the present disclosure.
Figure 9:
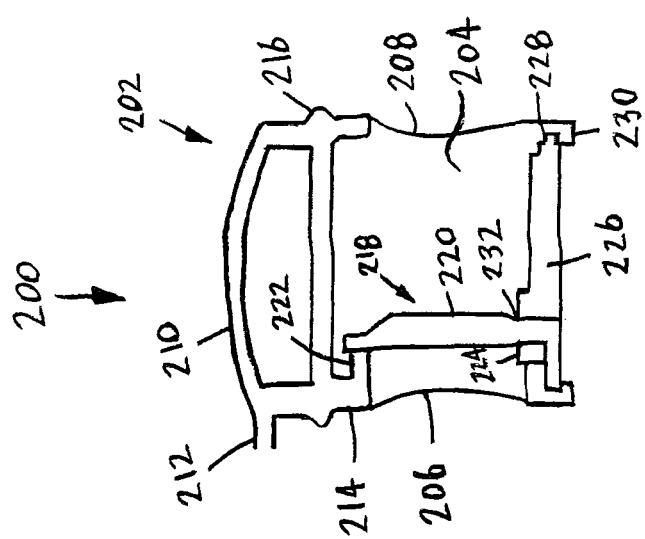
FIG. 9 is a partial cross-sectional view of another embodiment of a disposable turret having a check valve shown in a closed position constructed according to the present disclosure.

FIGS. 9 and 10 illustrate another embodiment of a disposable turret 200 constructed according to the present disclosure. The disposable turret 200 is shown in cross-section in both FIGS. 9 and 10. Also, the disposable turret 200 may replace the disposable turrets 10 and 100 and may be inserted into the valve body 50, as has been discussed. The disposable turret 200 comprises a rotatable valve sealing body 202 having a bore 204 having a tip receiving end opening 206 and a hose receiving end opening 208. The rotatable valve sealing body 202 also has a top 210 and a handle portion 212 connected to the top 210. Although not shown in this particular view, the disposable turret 200 also has an indentation formed in an exterior surface 214. An annular ridge portion 216 is formed near the top 210. The annular ridge portion 216 is capable of fitting into the channel 72 (FIG. 2) in a snap fit engagement to secure the disposable turret 200 in the valve body 50. The tip receiving end opening 206 has a check valve 218 positioned therein to selectively open or close the tip receiving end opening 206. The check valve 218 is provided for allowing liquid, saliva, or debris to pass from the tip receiving end opening 206, the check valve 218, the bore 204, and out the hose receiving end opening 208 when the check valve 218 is opened, as depicted in FIG. 10. The check valve 218 also prevents any liquid, saliva, or debris from passing or traveling from the hose receiving end 208, the bore 204, and through the check valve 218 when the check valve 218 is closed, as is illustrated in FIG. 9. The check valve 218 will close when a reduced pressure occurs from an interaction of a mouth of a patient on an evacuator tip device. As has been indicated, a patient may be requested to close the mouth of the patient around the evacuator tip device. When this occurs, a reduced pressure results in which a backflow may occur. The check valve 218 is sensitive to this pressure differential and will close to prevent backflow.

The check valve 218 has a flap portion 220 that seals against a top seat portion 222 and a bottom seat portion 224 that are formed in the body 202. The flap portion 220 is connected to a bottom plate member 226. The bottom plate member 226 snaps into an opening 228 formed in a bottom 230 of the body 202. The flap portion 220 may be connected to the bottom seat portion 224 by use of a hinge 232 or by any other suitable connection means. When manufacturing the body 202, the flap portion 220 is inserted into the opening 228 and then the bottom plate member 226 is snapped into place in the opening 228 in the bottom 230. The check valve 218 is inside the disposable turret 200 and offset from the tip receiving end opening 206.

In operation of for example the disposable turret 100, which has been inserted into the valve body 50, the hose receiving end 56 has one end of a suction hose secured thereon and the other end of the suction hose is connected to a suction system. The tip receiving end 54 has the rear end 64 of the evacuator tip device 60 inserted therein so that the rear end 64 is captured within the indentation 140 formed in surface 138 of the disposable turret 100. The disposable turret 100 is in a closed position at this point. The handle 112 may be moved to open the disposable turret 100 to allow air to flow through the valve body 50, the disposable turret 100, the check valve 118, and the evacuator tip device 60. The front end 62 of the evacuator tip device 60 may now be inserted into the mouth of a dental patient. The handle 112 may include an indicator to indicate the closed position and the open position of the disposable turret 100. Once in the open position, air is allowed to flow through the evacuator tip device 60, the check valve 118, the bore 108, the lumen 58, and into a suction system. In the event that reduced pressure occurs from an interaction of a mouth of a patient on the evacuator tip device 60, the check valve 118 will close and no backflow will be allowed from the suction system or the disposable turret 100. When suction is not needed during a dental procedure, the handle 112 is moved to the closed position. Further, once a dental procedure has been completed, the handle 112 is moved past the closed position so that the tab portion 162 forces the evacuation tip device 60 forwardly and the tab portion 160 contacts the tab portion 74 of the valve body 50 to force the valve sealing body 102 upwardly. The evacuation tip device 60 may now be remove and discarded. The disposable turret 100 is then easily separated from the valve body 50 and discarded since the turret 100 is disposable. The valve body 50 is removed from the suction hose and the valve body 50 is then cleaned and sanitized in any suitable manner. Once the valve body 50 has been processed, a new disposable turret 100 may be inserted into the valve body 50. With the new disposable turret 100 installed, another dental procedure may be initiated.

The disposable turrets 10, 100, or 200 may be formed of any suitable material such as plastic, polyethylene, and high density polyethylene or any other suitable material that is disposable and recyclable. Any suitable plastic may be used to construct the disposable turrets 10, 100, or 200 so that the turrets 10, 100, and 200 are strong enough to withstand use in a dental operation or procedure. It is also possible and contemplated to incorporate an antimicrobial agent or chemical in the plastic or to provide a coating of an antimicrobial agent on the plastic to further prevent cross-contamination when using the disposable turrets 10, 100, or 200. As can be appreciated, the antimicrobial agent may be incorporated into any of the components of the disposable turrets 10, 100, and 200. The disposable turrets 10, 100, and 200 are adapted to be inserted into the valve body 50. As has been indicated above, the valve body 50 may be constructed of metal and is suitable for numerous uses and cleanings.

From all that has been said, it will be clear that there has thus been shown and described herein a dental valve device having a disposable turret which fulfills the various advantages sought therefore. It will become apparent to those skilled in the art, however, that many changes, modifications, variations, and other uses and applications of the subject dental valve device having a disposable turret are possible and contemplated. All changes, modifications, variations, and other uses and applications which do not depart from the spirit and scope of the disclosure are deemed to be covered by the disclosure, which is limited only by the claims which follow.

What is claimed is:

1. A dental valve device comprising:
   a valve body having a tip receiving end, a hose receiving end, a lumen formed between the tip receiving end and the hose receiving end, an opening formed in the valve body; and
   a rotatable valve sealing body adapted to be inserted into the opening formed in the valve body, the rotatable valve sealing body having a bore for alignment with the lumen formed between the tip receiving end and the hose receiving end, the bore having a tip receiving opening and a hose receiving opening, a check valve, the rotatable valve sealing body having an outer surface having an indentation formed in the outer surface adjacent to the tip receiving end opening with the indentation having an upper ramp portion, a lower ramp portion, and an end having a tab portion.

2. The dental valve device of claim 1 wherein the rotatable valve sealing body is constructed of plastic.

3. The dental valve device of claim 1 wherein the indentation spans from the tip receiving end to the end.

4. The dental valve device of claim 1 wherein the check valve comprises a flap portion.

5. The dental valve device of claim 4 wherein the flap is movable between an opened position and a closed position.

6. The dental valve device of claim 4 wherein the valve body further comprises a tab portion and the handle portion of the rotatable valve sealing body further comprises a tab portion with the tab portion of the handle portion for contacting the tab portion of the valve body for removing the rotatable valve sealing body from within the opening of the valve body.

7. The dental valve device of claim 1 wherein an antimicrobial agent is incorporated into the rotatable valve sealing body and the check valve.

8. A dental valve device comprising:
   a valve body having a tip receiving end, a hose receiving end, a lumen formed between the tip receiving end and the hose receiving end, and an opening formed in the valve body; and
   a rotatable valve sealing body adapted to be inserted into the opening formed in the valve body, the rotatable valve sealing body having a bottom having an opening, a bore for alignment with the lumen formed between the tip receiving end and the hose receiving end, the bore having a tip receiving end opening and a hose receiving end opening, the rotatable valve sealing body having a check valve positioned in the bore and the opening in the bottom, the rotatable valve sealing body having an outer surface having an indentation formed in the outer surface adjacent to the tip receiving end opening with the indentation having an upper ramp portion, a lower ramp portion, and an end having a tab portion.

9. The disposable dental valve device of claim 8 wherein the check valve comprises a flap portion and a bottom plate member.

10. The disposable dental valve device of claim 9 wherein the rotatable valve sealing body further comprises a top seat portion and a bottom seat portion for the flap portion to seal against.

11. The disposable dental valve device of claim 8 wherein the rotatable valve sealing body is constructed of plastic.

12. The disposable dental valve device of claim 8 wherein the check valve is constructed of plastic.

13. The disposable dental valve device of claim 8 wherein an antimicrobial agent is incorporated into the disposable turret.

14. The disposable dental valve device of claim 8 wherein the check valve comprises a flap portion that seals against a top seat portion and a bottom seat portion that are formed in the rotatable valve sealing body, the flap portion being connected to a bottom plate member with the bottom plate member for snapping into the opening formed in the bottom of the rotatable valve sealing body.

* * * * *